(12) United States Patent
Kojima (10) Patent No.: US 6,599,876 B2
(45) Date of Patent: Jul. 29, 2003

(54) MEDICAMENT AND METHOD FOR TREATING RENAL DISEASE

(75) Inventor: Itaru Kojima, Maebashi (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/820,857

(22) Filed: Mar. 30, 2001

(65) Prior Publication Data
US 2002/0028762 A1 Mar. 7, 2002

(30) Foreign Application Priority Data
Mar. 31, 2000 (JP) .......................................... 2000-097553

(51) Int. Cl.⁷ .......................... A61K 38/00; C07K 14/00; A61P 5/00; C12N 15/00; C12N 15/09
(52) U.S. Cl. .......................... 514/2; 530/300; 530/399; 435/7.1; 435/69.1; 435/440
(58) Field of Search .................. 530/300, 398; 514/2; 424/278.1, 451, 489, 490, 492

(56) References Cited

FOREIGN PATENT DOCUMENTS

WO    WO 97/15321    5/1997

OTHER PUBLICATIONS

Shiozaki, M. et al (1992) "The existence of activin A / erythroid differentiation factor and its inhibitor in human serum: compariso of normal and chronic renal failure sera" Biochem. Biophys. Com. vol. 183, pp. 273–279.*

Kogure, K. et al (1998) "Immediate onset of DNA synthesis in remnant rat liver after 90% hepatectomy by an administration of follistatin" J. Hepatol. vol. 29, pp. 977–984.*

Lee, S.–L. et al "Regulation of mystatin activity and muscle growth" Prec. Natl. Acad. Sci. U.S.A. vol. 98, pp, 9306–9311.*

K. Kogure, et al., Hepatology, vol. 24, No. 2, pp. 361–366, "Intravenous Administration of Follistatin: Delivery to the liver and effect on liver regeneration after partial hepatectomy", Aug. 1996.

Akito Maeshima, et al., "Involvement of the Activin–Follistatin System in Tubular Regeneration after Renal Ischemia in Rats", J Am Soc Nephrol 12(2001, pp. 1685–1695).

* cited by examiner

*Primary Examiner*—Karen Cochrane Carlson
*Assistant Examiner*—Samuel Wei Liu
(74) *Attorney, Agent, or Firm*—Oblon, Spivak, McClelland, Maier & Neustadt, P.C.

(57) ABSTRACT

A medicament for treating a renal disease, comprising a therapeutically effective amount of an activin inhibitor as an active ingredient. Also, a method for treating a renal disease, comprising administering a therapeutically effective amount of an activin inhibitor to a patient suffering from renal disease is disclosed. The activin inhibitor may be follistatin, an anti-activin antibody, an inhibitor to activin receptor or an anti-activin receptor antibody, an inhibitor to signal transduction relating to activin receptor, an activin production inhibitor in kidney, and the like.

13 Claims, 6 Drawing Sheets

MEDICAMENT AND METHOD FOR TREATING RENAL DISEASE

BACKGROUND OF THE INVENTION

1. Field of the Invention

The present invention relates to a medicament useful for treating renal disease and to a method for treating renal disease by administration of such a medicament.

2. Description of the Related Art

Follistatin, a protein having the ability of binding to activin, has been discovered with reference to the activity of cultured pituitary gland cells to promote the production of follicle stimulating hormone (FSH) (Esch, F. S. et al., *Mol. Endocrinol.;* 1(11): 849–55 (1987). In the early stage of the study, it was found that follistatin inhibited the secretion of FSH. This suggested that follistatin will have a reverse activity with respect to activin, which promotes the secretion of FSH. Subsequent studies revealed that follistatin is a specific binding protein for activin that specifically binds to activin and inhibits its activity (Nakamura, T. et al., *Science,* 247 (4944): 836–08; (1990)). Several kinds of activin such as activin homdimer βAβA, activin heterodimer βAβB, activin homdimer βBβB, and the like occur in organisms, and follistatin is known to have inhibitory activity to any one of these activins (Fukui, A. et al., *Dev. Biol.,* 159(1): 131–139 (1993), Sugino, H. et al., *Seikagaku,* 68(8): 1405–1428 (1996)).

As a result of further studies on follistatin, the gene encoding it has been isolated and its amino acid sequence has also been reported (WO89/01945, Shimasaki, S., et al., *Proc. Natl. Acad. Sci. USA,* 85(12): 4218–22 (1988)).

Follistatin is known to have a pharmacological effect of promoting the cell growth of liver upon its topical administration (Kogure, K. et al., *Hepatology,* 24(2): 361–6 (1996), Kojima, I., *BIO Clonica,* 883(12), 43–46 (1997)). Also, it is reported that an antagonist of follistatin promotes cure of wounds and fibrous disorders with less cicatrization (WO97/15321). However, it has not yet been known that follistatin is effective in the therapy of renal diseases.

Heretofore, steroid preparations, prostaglandin preparations, hypotensive diuretic preparations and the like have been used as the medicament for treating renal diseases. However, the known medicaments are insufficient for radical cure.

DETAILED DESCRIPTION OF THE INVENTION

An object of the present invention is to provide a medicament for treating a renal disease that has different activity from that of conventional medicaments for treating renal diseases and enables effective treatment.

Another object of the present invention is to provide a method for treating a renal disease using such a medicament for treating a renal disease.

The present inventors have made extensive study with a view to solving the aforementioned problems, and as a result they have found that the expression of follistatin decreases in kidney having a disease. Also, paying attention to activin that presumably is associated with the growth of kidney cells and the function thereof, they have demonstrated by use of follistatin that inhibition of the activity of activin enables promotion of the proliferation of kidney cells. The present invention is thus completed based on this finding.

That is, the present invention provides a medicament for treating a renal disease, comprising a therapeutically effective amount of an activin inhibitor as an active ingredient.

Further the present invention provides the medicament used in treating renal disease with which activin activity is associated.

Further the present invention provides the medication where the activin inhibitor may be follistatin.

Further the present invention provides a method for treating a renal disease, comprising administering an activin inhibitor to a patient suffering from renal disease.

The biological reaction observed as the phenomenon of regeneration of tissue, that is, reconstruction of tissue is highly homologous with the phenomena such as differentiation, proliferation or migration of cells in organogenesis in the process of development and a common fluid factor may participate in both mechanisms.

Some growth factors in the organogenesis of kidney, whose representative examples include a hepatic cell growth factor (HGF) that is an indispensable differentiation inducing factor, reportedly promote each the proliferation of or inhibits apoptosis of uriniferous tubule cells in the regeneration of uriniferous tubule in kidney, that is regeneration of uriniferous tubule epithelium in various acute renal failure models (e.g., ischemia, nephrotoxic substances, etc.) to alleviate the renal functional disorder. As a result of studies thus far made, it can be anticipated that activin and follistatin are important differentiation inducing factors in the process of development of kidney and at the same time play a certain role in the phenomenon of regeneration based organ culture using a renal primordium, an in vitro model of lumen formation using MDCK cells (kidney from a female cocker spaniel, or phenotype of a transgenic mouse (Maeshima, A. et al., *Biochem. Biophys. Res. Commun.,* 268(2):445–9 (2000)). On the other hand, further studies are being progressed to elucidate that the role of activin and follistatin is a control mechanism of the initiation and termination of liver regeneration subsequent to hepatectomy of the liver (Kogure, K. et al., *Hepatology,* 24(2): 361–6 (1996), Kojima, I., *b BIO Clonica,* 883(12), 43–46 (1997)). Hence, the present inventors have made further study on the role of activin and follistatin in the regeneration of uriniferous tubule in kidney using an ischemic acute renal failure model.

The results of the above study suggest that changes in the expression of activin and follistatin observed after the ischemia/reperfusion of the liver will play some role in the regeneration of uriniferous tubule, as will be apparent from the examples described hereinbelow. That is, 48 hours after the ischemia/reperfusion, the expression of activin is exalted while the expression of follistatin, an antagonist against activin, is decreased. This suggests that activin is functionally in an activated state even temporarily. At present, it is unclear as to what significance such changes in the expressions of activin and follistatin will have in the regeneration of uriniferous tubule. However, in the studies on other organs thus far made, that is, regeneration phenomena in a brain ischemia model and a skin repairing model, it has been observed that the expression of activin is induced, and activin participates in the production of extracellular matrix and fibrosis of tissues. This suggests that activin may possibly participate in the prolongation of tissue disorder in a similar mechanism to that observed in kidney.

Accordingly, the present inventors have made a further study as to what an influence is given to the degree of uriniferous tubule regeneration and tissue disorder by administering follistatin, an antagonist against activin, to inhibit the activity thereof, and they have elucidated that the administration of follistatin results in a significant increase in cell number.

The foregoing results suggests that activin and follistatin may be important differentiation inducing factors in the process of development and regeneration of kidney and may have some role in the onset mechanism of the following pathology.

(1) Onset Mechanism of Uriniferous Tubule/Interstitial Tissue

Since tubulointerstitial disorder has a stronger correlation with the prognosis of a renal function than a glomerulus disorder, recently studies on the onset mechanism of a tubulointerstitial disorder are being progressed. The causes of the disorder include an ischemia/reperfusion disorder, a postrenal disorder, a drug-induced disorder as well as secondary causes that occur subsequent to the glomerulus disorder. Factors for developing such disorders include invasion of cells into the interstitial tissue, fibrosis of interstitial tissue, transformation of uriniferous tubule/interstitial cells, and the like.

The uriniferous tubule, like an ovary, is one of the tissues that express follistatin in largest amounts among all the organs in the body and hence it is presumed that follistatin be present in order to maintain the structure and function of uriniferous tubule structure not only in regeneration but also in a uriniferous tubule/interstitial tissue disorder.

(2) Inhibition of the Progress of Chronic Renal Failure

One reason for chronic renal failure is considered to be due to continuous accumulation of extracellular matrix such as sclerosis of glomerulus or fibrosis of interstitial tissue during its progress. Also, in decreasing the number of patients who are subjected to dialysis and who tend to increase in number year after year, it is one of important objects in the therapy of renal diseases to delay the progress of renal failure. Hitherto, reportedly activin participates in the fibrosis of tissues, such that the expression of activin exalts in cirrhosis or fibroid lung to induce production of collagen or exalt production of Type I collagen in renal fibroblast (Matsuse, T., Nihon *Kokyuki Gakkai Zasshi*, 36(5): 413–20 (1998), Sugiyama, M., *Gastroenterology*, 114(3): 550–8 (1998)).

Extracellular matrix exists in order to construct tissues/organs in development/differentiation and is qualitatively/quantitatively controlled so that the differentiated character of the cell can be maintained and at the same time it functions as an important factor in various diseases, in particular in fibrosis of tissues. Since activin is anticipated to be an important controlling factor in the production of extracellular matrix, there is the possibility that activin, like transforming growth factor β (TGF-β) or the like, will participate in the progress of disease in the development of from various renal diseases (chronic glomerular nephritis, diabetic nephropathy and the like) to a chronic renal failure. Conversely, it is possible to study strategy of the treatment for inhibiting the progress by use of follistatin, an antagonist. For example, it may possible to delay the progress of a renal failure while maintaining the function of uriniferous tubule to some extent by quantitatively or functionally increasing the uriniferous tubule/interstitial tissue region that has not reached to fibrosis yet in a chronic renal failure by use of follistatin.

(3) Others

Since production of follistatin is observed not only in uriniferous tubule cells but also in mesangium cells, activin is presumed to participate in the proliferation and differentiation of cells in various diseases in which glomerular nephritis or mesangium cells participate.

Hereinafter, the present invention will be described in detail.

The medicament for treating a renal disease according to the present invention contains an activin inhibitor as an active ingredient. In the present invention, by the term "activin inhibitor" is meant a substance that decreases or destroys the physiological function that activin has. It may be the one that directly couples with activin to inhibit the physiological function of activin or may be the one that inhibits the production of activin itself. Alternatively, it may be the one that inhibits the signal transduction generated by the coupling of activin with an activin receptor.

Specific examples of activin inhibitor include follistatin, an anti-activin antibody, an inhibitor to activin receptor or an anti-activin receptor antibody, an inhibitor to signal transduction relating to activin receptor, an activin production inhibitor in kidney, and the like. The inhibitor to activin receptor includes proteins or compounds having structures similar to that of follistatin and blocks the activin receptor to inhibit the coupling of activin with follistatin. The activin production inhibitor includes antisense DNA to the activin gene and the like.

The action of activin inhibitor can be examined by measuring the activity of activin in the presence or absence of an activin inhibitor. The activity of activin can be measured by in vitro tests using as an index a differentiation inducing action to erythroblasts (EDF assay: Eto, Y. et. al., *Biochem. Biophys. Res. Commun.*, 142(3): 1095–103 (1987)) or a follicle stimulating hormone secretion promoting action to pituicytes, or the like.

In the present invention, the follistatin is not particularly limited and any follistatin may be used regardless of the type or origin of it as far as it has an activin inhibiting action. For example, as far as it has an activin inhibiting action, it may be the one originated from an animal such as a pig as well as human follistatin, or natural type follistatin or recombinant type follistatin.

It is known that follistatins are glycoproteins whose peptide moiety has a molecular weight of from 30,000 to 40,000 differing in amino acid residue number, e.g., 315, 303, or 288 and in the site and number of attachment of sugar chains. If they have other structural changes than described above, the effect of the present invention can be obtained as far as they have the ability of coupling with activin and retain an equivalent activin inhibitory activity as the activin coupling protein.

The natural type follistatin may be prepared by extracting it from an organ of animal, such as an ovary, and subjecting it to a purification step. Recombinant type follistatin can be prepared by introducing human or animal follistatin cDNA into a suitable expression vector, followed by gene transfer into a suitable animal cell with the vector, cultivating the cells and subjecting the culture medium to a purification step.

The recombinant follistatin can be prepared by a method for producing a heterologous protein by an ordinary recombinant technique using a DNA encoding follistatin. The DNA encoding follistatin and the method of producing a recombinant follistatin using the DNA are disclosed in WO89/01945. In the example described hereinbelow, the follistatin used was purified from the culture medium of CHO cells having incorporated therein cDNA corresponding to human follistatin composed of 315 amino acids.

The medicament for treating renal diseases according to the present invention is provided as a medicament in the form of a pharmaceutical composition comprising an activin inhibitor, such as follistatin, alone or an activin inhibitor and a pharmaceutically acceptable additive. The activin inhibitor may be used alone, or a plurality of activin inhibitors may be used in combination. Alternatively, drugs used as active ingredients of conventionally used medicaments for treating renal diseases may be blended together with the activin inhibitor.

The formulation of the medicament for treating renal diseases according to the present invention includes, injections, sublingual agents, percutaneous poultices, tablets, capsules, granules, syrups, suppositories, ointments, eye drops, and the like. Of these, injections, sublingual agents, and percutaneous poultices are preferred. Pharmaceutically acceptable excipients such as lactose, potato starch, calcium carbonate, and sodium alginate may be compounded depending on the formulation. Other materials used in ordinary preparations, for example proteins such as serum albumin, salts for buffering action or controlling osmotic pressure, carriers, excipients and the like components may be blended. In the case of injections, distilled water for injection, physiological saline, Ringer's solution and the like may be used. A dispersant may be added thereto.

The dosage of the medicament for treating renal diseases according to the present invention where follistatin is used as the activin inhibitor may be generally from 0.1 $\mu$g/kg to 10 mg/kg, preferably 1 $\mu$g/kg to 1 mg/kg of follistatin by intravenous administration for an adult for 1 day although the dosage may vary depending on the age, symptom and the like of the patient.

The medicament for treating renal diseases according to the present invention is useful in the therapy and prevention of renal diseases and such renal diseases include those renal diseases in which exaltation of activin action is considered to participate, for example, acute renal failure, chronic renal failure, glomerular nephritis, diabetic nephropathy and the like. However, the present invention is not limited thereto and can be applied to various renal disorders widely.

BEST MODE FOR CARRYING OUT THE INVENTION

Hereinafter, the present invention will be described in more detail by examples. However, the present invention is not limited thereto.

EXAMPLE 1

Figure 1:
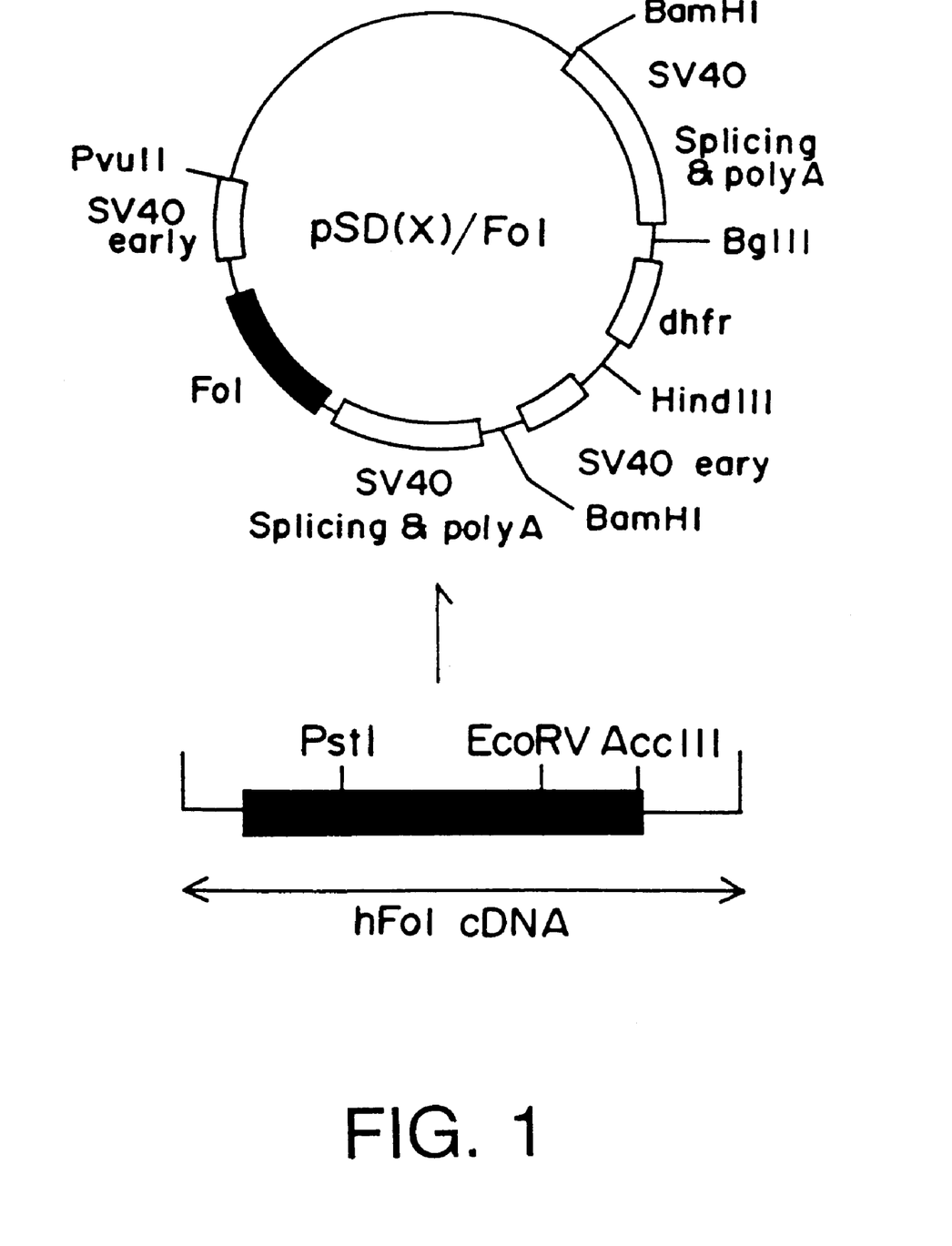
FIG. 1 is a diagram illustrating the structure of a human follistatin cDNA expression vector.

Using the method described in the literature Onomichi, K. et al., *J. Biochem* (Tokyo); 2(1): 123–31 (1987)), the human follistatin cDNA described in the literature Shimasaki, S. et al., *Proc. Natl. Acad. Sci. USA*, 85(12): 4218–22 (1988)) was inserted in an animal cell expression vector to make plasmid pSD(X)/Fol shown in FIG. 1. The pSD(X)/Fol was introduced into CHO-DHFR deficient cell (Chinese hamster ovary cell dihydrofolic acid reductase defective strain) by the method described in the literature Murata, et al., *Biochem. Biophys. Res. Commun.*, 151(1): 230–5 (1988)) using a calcium phosphate method. After cultivating the transgenic cells in a selective medium containing 0.1 $\mu$M MTX (mesotrexate) for 2 weeks, culture medium was exchanged with a fresh medium, followed by continuing the cultivation for further 1 week to obtain resistant cells. The cells were transferred into a selective medium containing 0.5 $\mu$M MTX to obtain resistant cells. Subsequently, similar operations were repeated with increasing the concentration of MTX stepwise, to finally obtain 40 $\mu$M MTX-resistant cells.

Figure 2:
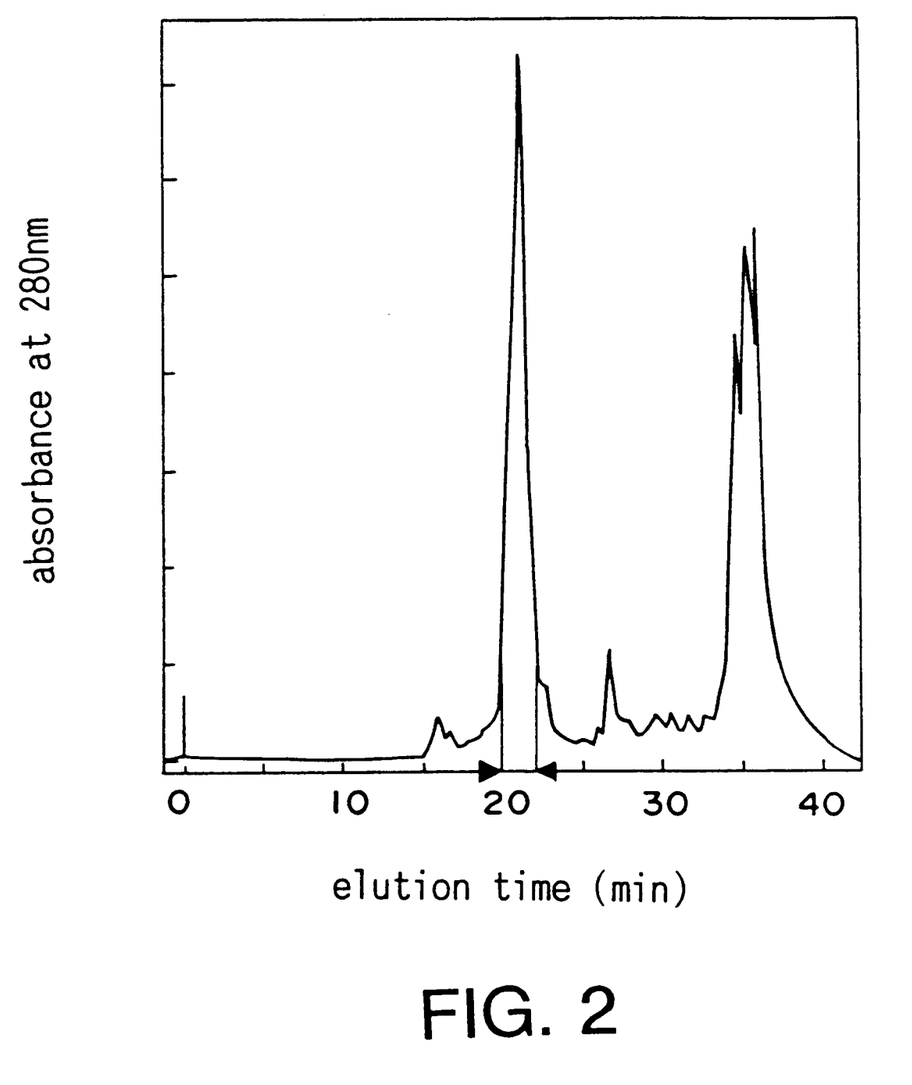
FIG. 2 is a diagram illustrating purification of follistatin using high performance liquid chromatography (HPLC). The vertical axis indicates absorbance ($OD_{280}$) and the horizontal axis indicates elution time (minute). The recombinant type human follistatin was eluted at the site indicated by an arrow.
Figure 3:
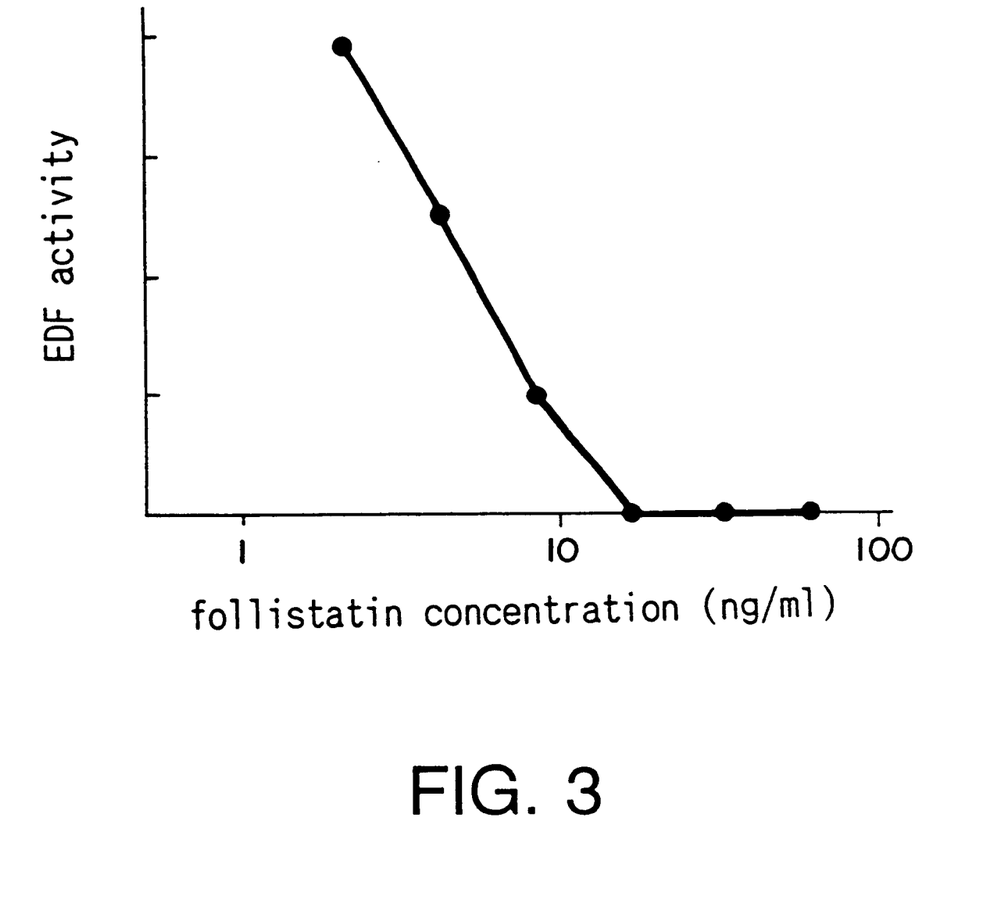
FIG. 3 is a diagram illustrating the activin inhibitory activity of purified follistatin. The inhibitory activity to 5 ng/ml activin A was measured using EDF assay. The vertical axis indicates EDF activity and the horizontal axis indicates follistatin concentration. The size of each group is n=6.

From these cells was separated a clone by a single cell separation method, and its follistatin production amount was measured using an activin neutralization activity as an index. The activin activity was measured using EDF assay, in which an inhibitory activity against the activity of 5 ng/ml activin A (EDF) prepared by the method described in the literature (Eto, Y. et al., *Biochem. Biophys. Res. Commun.*, 142(3): 1095–103 (1987)) was determined. The clone that showed the highest production amount was selected and cultured in a roller bottle to obtain about 10 liters of the culture solution. After concentrating it 5 folds by an ultrafiltration membrane (MW 5000 cut-off, produced by Millipore), the concentrate was charged in a 50% PBS-equilibrated heparin column (70 ml bed volume). After washing with 50% PBS, the column was eluted with 50% PBS containing 1.5 M NaCl and the protein eluted fractions were separated under UV monitoring. The 1/5 volume of the fractions was fractionally eluted with an acetonitrile concentration gradient by using HPLC (YMC Pack S-10 834/20 mm). FIG. 2 shows the elution pattern. The fraction sandwiched by the arrows was taken and after lyophilization, dissolved in a small amount of distilled water to obtain purified follistatin. The amount of protein of the purified follistatin was calculated from the HPLC absorbance. FIG. 3 shows an activin inhibitory activity of the purified follistatin.

EXAMPLE 2

The both side renal arteries of male Wistar rats were clamped for 45 minutes, then opened to make ischemia/reperfusion models. After the aforementioned treatment, kidneys were extirpated chronologically, and the expressions of activin $\beta$A subunit and of follistatin were examined by RT-PCR (Vukicevic, S. et al., *J. Clin. Invest.*, 102(1): 202–214 (1998)) and Northern blotting (Zhang, Y. Q. et al., *Hepatology*, 25(6): 1370–1375 (1997)), respectively. The localization of follistatin mRNA in the renal tissue was studied by in situ hybridization (Suzuki, M. et al., *Diabetes*, 46(9): 1440–1444 (1997)).

As a result, substantially no expression of the activin $\beta$A subunit was detected in kidneys of normal rat and of sham group rat. In contrast, in the ischemia/reperfusion models, its expression is exalted after 12 hours from the ischemia/reperfusion treatment and it lasted after 120 hours. On the other hand, follistatin expressed in large amounts in kidneys of normal rat and of sham group rat, while in the ischemia/reperfusion models, the expression shows a temporary decrease with the peak at 48 hours from the ischemia/reperfusion treatment and recovers thereafter to the original level.

As a result of the in situ hybridization, the expression of mRNA was localized to the uriniferous tubule cells in the outer layer of the medulla and after the ischemia/reperfusion, the signal weakens in accordance with the result of the Northern blotting; the expression was decreased not only in necrotic tissues but also in morphologically normal uriniferous tubule cells.

EXAMPLE 3

To the ischemia/reperfusion models made in the same manner as in Example 2 was administered 3 μg of follistatin (administered group) or physiological saline (control group) in a single dose from the tail vein within 30 minutes after the ischemia/reperfusion treatment. Then, kidneys were extirpated chronologically. The histological change was evaluated by PAS staining and the degree of renal regeneration was evaluated by BrdU (bromodeoxyuridine) staining. The histological change and degree of renal regeneration were compared between the follistatin administered group and control group.

Figure 5:
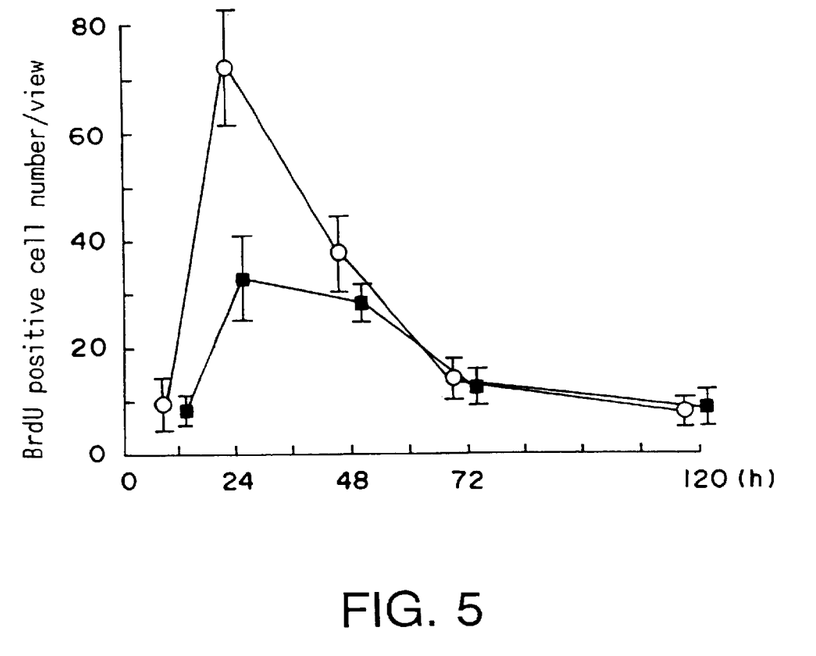
FIG. 5 is a diagram illustrating chronological change in promotion of renal cell proliferation with follistatin. The vertical axis indicates BrdU (bromodeoxyuridine) positive cell number and the horizontal axis indicates time after the administration. "○" stands for follistatin administered with follistatin and "●" stands for control group. In each group, n=6.

As a result, in the control group, the DNA synthesis temporarily increased with a peak at 48 hours (BrdU staining: FIG. 5). Further, BrdU-positive cells were observed mainly in the uriniferous tubule cells in the outer layer of the medulla that is damaged by the ischemia. On the other hand, in the follistatin-administered group, the positive cells significantly increased as compared with the control group (FIG. 5). The BrdU-positive cells were observed not only in the outer layer of the medulla but also in the uriniferous tubule in the cortex. Histologically, in the control group, necrosis of uriniferous tubule, expansion of uriniferous tubule lumen, hemostasis and the like were observed accompanying the tissue damages due to ischemia while in the follistatin administered group, these symptoms were light as compared with the control group.

Figure 4:
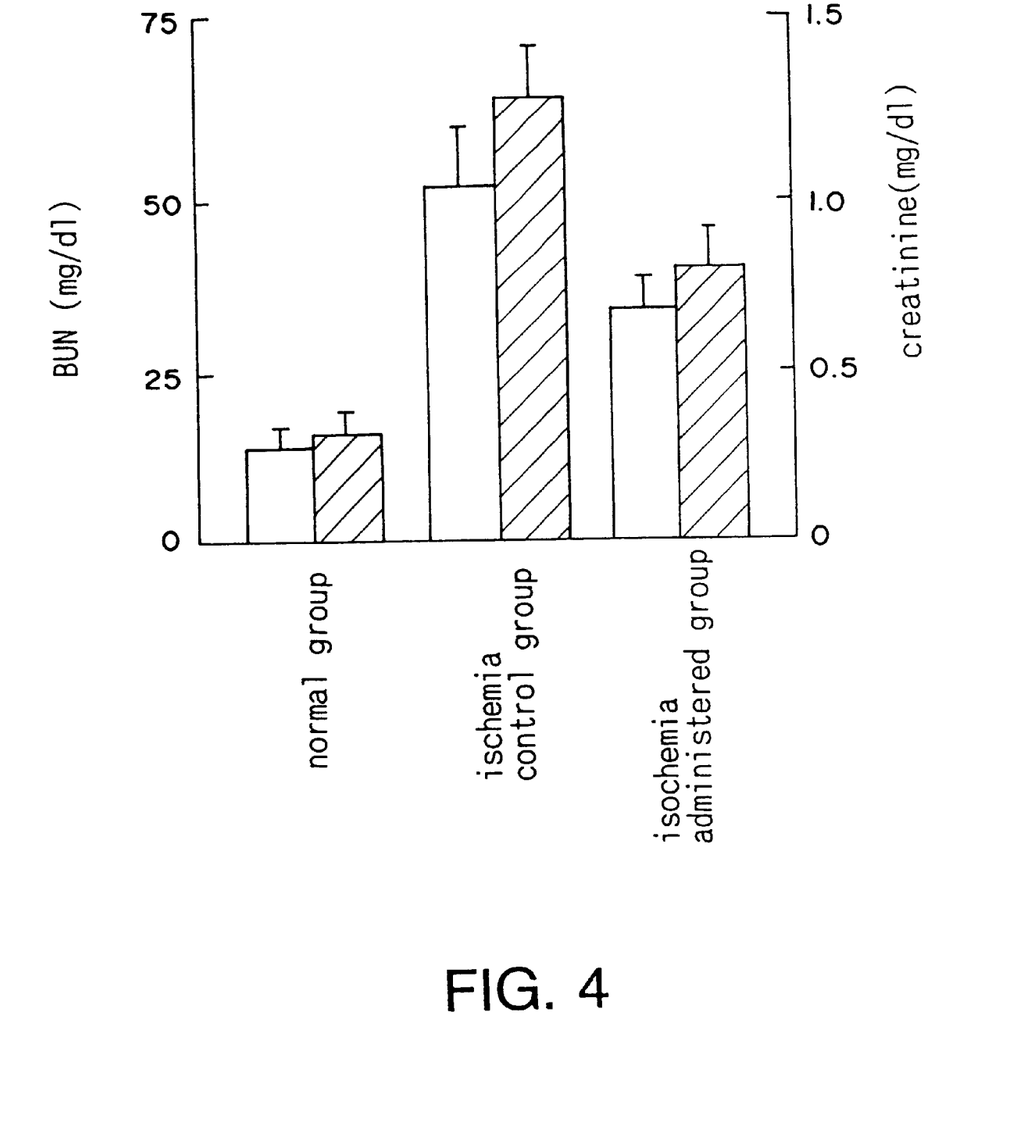
FIG. 4 is a diagram illustrating the improvement of renal disorder by means of follistatin. In the vertical axis, "□" indicates BUN (blood urea nitrogen) and "■" indicates creatinine concentration.
Figure 6:
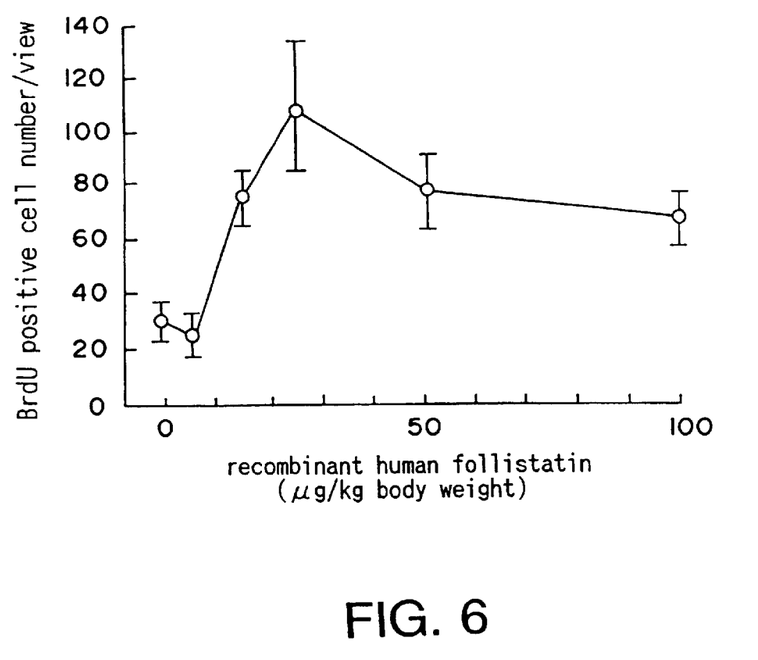
FIG. 6 is a diagram illustrating dose-response characteristics in renal cell proliferation promotion with follistatin. The vertical axis indicates BrdU positive cell number and the horizontal axis indicates the follistatin administration amount.
Figure 7:
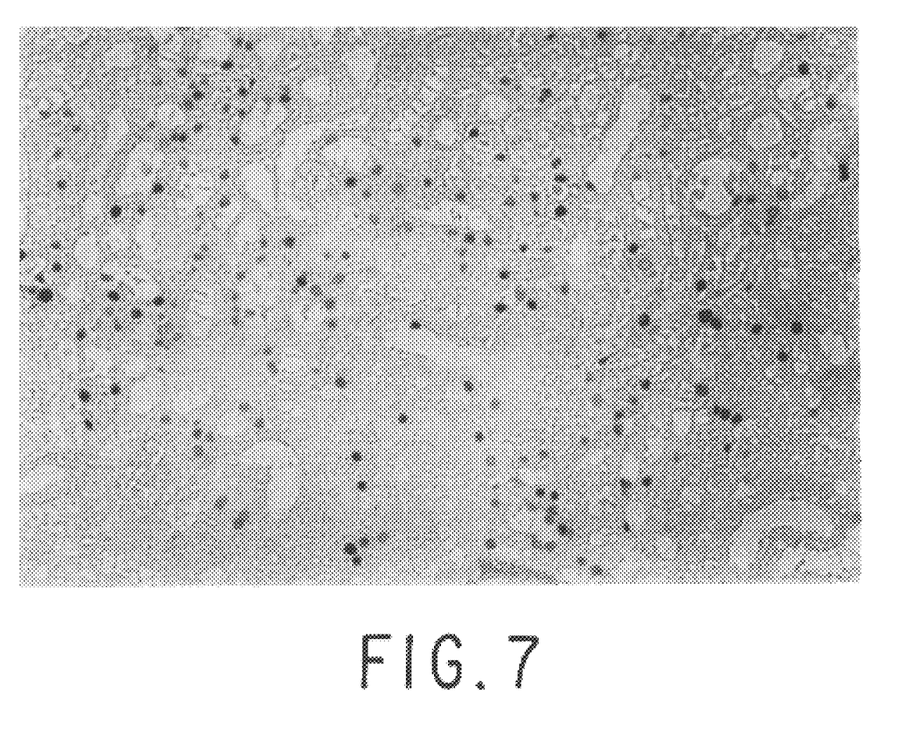
FIG. 7 is a photograph showing BrdU uptake by renal cells of a follistatin-administered rat.

As shown in FIG. 4, the rats administered with 3 μg of follistatin, the blood BUN (blood urea nitrogen) and creatinine amount after 24 hours decreased as compared with the non-administered group, which demonstrated that the renal function was improved. FIG. 6 illustrates the results of uptake of BrdU in the measurement of BrdU-positive cells after 24 hours from the administration of follistatin. As illustrated, the effect was observed with an administration amount of about 10 μg/kg or more, and the maximum activity was maintained with an administration amount of 20 μg/kg or more.

As described above, the administration of follistatin promoted regeneration of uriniferous tubule after an ischemic acute renal failure, which demonstrates the function of follistatin as a factor for promoting the regeneration of uriniferous tubule. At the same time, the administration of follistatin also induced DNA synthesis in cortex uriniferous tubule that is thought to be free of damages. This suggests the possibility that follistatin not only promotes regeneration but also exhibits some activity on uriniferous tubule cells in an intact state. The information will be important in considering therapeutic strategy against various uriniferous tubule/interstitial tissue disorders.

What is claimed is:

1. A method for treating a renal disease associated with increased activin activity, comprising administering to a patient in need thereof an effective amount of an activin inhibitor.

2. The method for treating the renal disease according to claim 1, wherein said activin inhibitor is follistatin.

3. The method according to claim 1, further comprising a pharmaceutically acceptable additive.

4. The method according to claim 1, wherein said effective amount of an activin inhibitor is in a formulation selected from the group consisting of injection form, sublingual agent form, percutaneous poultice form, tablet form, capsule form, granular form, syrup form, suppository form, ointment form, and eye drop form.

5. The method according to claim 1, wherein said effective amount of an inhibitor is in a formulation selected from the group consisting of injection form, sublingual agent form, and percutaneous poultice form.

6. The method according to claim 1, wherein said effective amount of an activin inhibitor is from 0.1 μg/kg to 10 mg/kg per day.

7. The method according to claim 1, wherein said effective amount of an activin inhibitor is from 1 μg/kg to 1 mg/kg per day.

8. The method according to claim 1, wherein the renal disease is selected from the group consisting of acute renal failure, chronic renal failure, glomerular nephritis, and diabetic nephropathy.

9. The method according to claim 8, wherein the renal disease is acute renal failure.

10. The method according to claim 8, wherein the renal disease is chronic renal failure.

11. The method according to claim 8, wherein the renal disease is glomerular nephritis.

12. The method according to claim 8, wherein the renal disease is diabetic nephropathy.

13. The method according to claim 2, wherein said follistatin is a pig follistatin, a human follistatin, or a recombinant follistatin.

* * * * *